United States Patent [19]

Greene

[11] Patent Number: 4,969,911
[45] Date of Patent: Nov. 13, 1990

[54] ADJUSTABLE PROSTHETIC JOINT WITH ALIGNMENT MEANS

[75] Inventor: Ted J. Greene, La Canada, Calif.

[73] Assignee: United States Manufacturing Company, Pasadena, Calif.

[21] Appl. No.: 453,080

[22] Filed: Dec. 19, 1989

Related U.S. Application Data

[63] Continuation of Ser. No. 312,126, Feb. 17, 1989, abandoned.

[51] Int. Cl.[5] ............................ A61F 2/62; A61F 2/76
[52] U.S. Cl. .......................................... 623/38; 623/27
[58] Field of Search ...................... 403/83, 84; 623/38; 33/534; 273/79

[56] References Cited

U.S. PATENT DOCUMENTS

| | | | |
|---|---|---|---|
| 679,261 | 7/1901 | Johnson | 33/534 |
| 3,206,235 | 9/1965 | Albinson | 623/38 |
| 3,273,168 | 9/1966 | Gardner | 623/38 |
| 3,659,294 | 5/1972 | Glabiszewski | 623/38 |
| 3,795,053 | 3/1974 | Burke | 33/534 |
| 3,982,278 | 9/1976 | May | 623/38 |
| 4,536,898 | 8/1985 | Palfray | 623/38 |
| 4,676,800 | 6/1987 | Chen | 623/38 |

FOREIGN PATENT DOCUMENTS

| | | | |
|---|---|---|---|
| 2605644 | 9/1976 | Fed. Rep. of Germany | 623/38 |
| 0321251 | 11/1971 | U.S.S.R. | 623/38 |
| 1026803 | 7/1983 | U.S.S.R. | 623/38 |

Primary Examiner—Randall L. Green
Assistant Examiner—David H. Willse
Attorney, Agent, or Firm—Christie, Parker & Hale

[57] ABSTRACT

A link between members of a prosthetic limb, such as a connector between a knee joint and an elongated artificial leg member, has a frustopyramidal four-sided boss divergingly projecting from a spherically convex base which slidably engages a correspondingly concave annular socket surrounding the boss. Two pairs of set screws set 90° apart in the annular socket are tightened against the sides of the frustopyramidal boss to enable its adjustment within a swing angle in two mutually orthogonal planes defining posterior-anterior positioning and lateral-medial positioning of the component parts of the prosthetic joint. The joint includes indexing means on a portion of one part visible for comparison of its angular position relative to the other part. The indexing means indicate relative position of the component parts in a plane that sets posterior-anterior position and in a separate plane that sets the lateral-medial position of the device. Further indexing means can indicate the relative rotation of one part with respect to the other part about a substantially vertical axis through the joint.

13 Claims, 3 Drawing Sheets

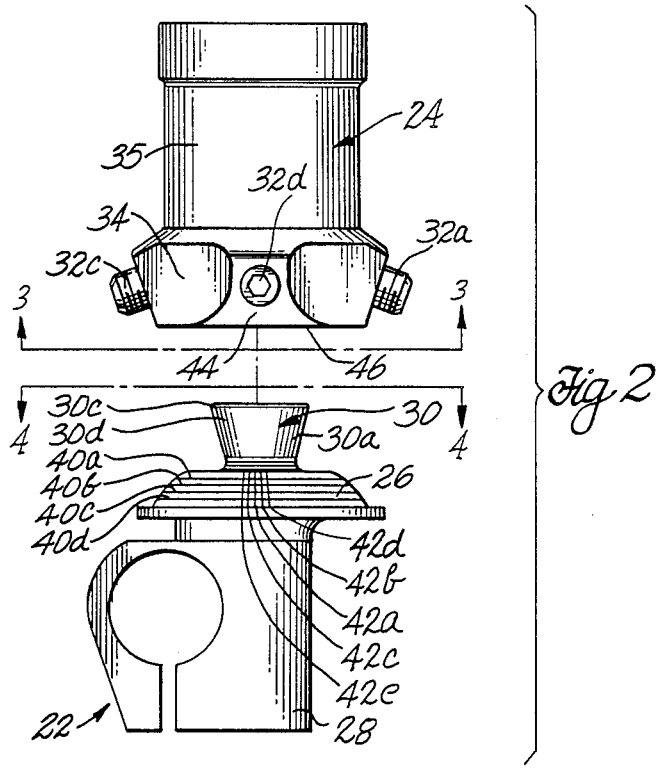
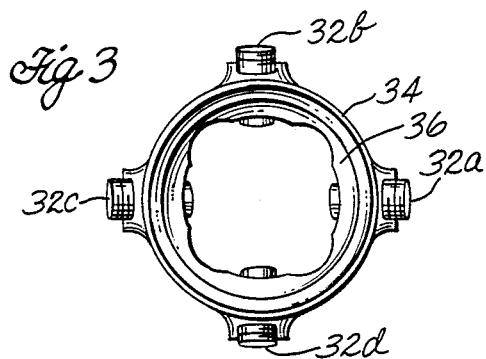
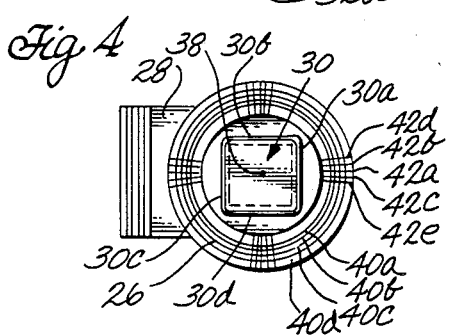

ADJUSTABLE PROSTHETIC JOINT WITH ALIGNMENT MEANS

CROSS-REFERENCE TO RELATED APPLICATIONS

This is a continuation of application Ser. No. 312,126, filed Feb. 17, 1989, now abandoned.

FIELD OF THE INVENTION

This invention relates to an adjustable prosthetic joint that forms a link between members of a prosthetic limb. More particularly, the invention relates to a prosthetic joint having means on it for use in aligning and realigning components of the joint.

BACKGROUND OF THE INVENTION

Prosthetic joints comprise an adjustable link designed to interconnect adjoining members of a prosthetic limb. By way of example, an adjustable prosthetic link can be used to interconnect adjoining prosthetic members such as a stump support and a thigh member, a knee joint and a member forming a lower leg, or at the ankle of the prosthetic device for connecting the lower end of a lower leg member and an artificial foot. Other examples of uses of adjustable prosthetic joints are known to those skilled in the art.

In a prosthetic leg, for example, the body structure of the user and his attitude when standing or walking may require certain adjustments in the relative position of various components in the artificial leg. Frequently, these adjustments must be made in two mutually orthogonal planes: in the anterior-posterior plane and in the lateral-medial plane. In the prior art, the use of a universal joint of the ball and socket type for this purpose was inconvenient because it provided no stability against rotation about the major axis of the limb. Once dislodged, the assembly could not be accurately returned to its original position without the help of external references.

On the other hand, prior attempts at solving the problem by a cross hinge articulation resulted in cumbersome and relatively expensive structures.

U. S. Pat. No. 3,659,294 to Glabiszewski, assigned to Otto Bock of West Germany, discloses a very successful prosthetic link mechanism for enabling relative adjustment of two members of a prosthetic limb in two mutually orthogonal planes, while avoiding the disadvantages then prevalent in the prior art.

The Otto Bock adjustable prosthetic link included a male and female part, respectively, on two artificial limb members to be relatively adjusted, one of the parts having two pairs of contact surfaces which are bisected by mutually orthogonal planes, the other part having adjustable abutment means such as set-screws engaging these surfaces for retaining the two parts in a selected angular position within predetermined swing ranges in the two planes. More specifically, the male part had a spherically convex base from which a substantially frustopyramidal boss rises divergingly and the female part comprised an annular socket. The contact surfaces on the male part comprised the respective sides of the preferably four-sided frustopyramid. The set-screws bearing upon these sides extended at right angles and were lodged in the socket for engaging the contact surfaces of the boss for retaining the component parts in a selected angular position within predetermined swing ranges.

This adjustable link has been used for a number of years as a means for setting the angular relationship between component parts at various joints in a prosthetic limb. However, adjustment and readjustment of this link and other prosthetic components can be a cumbersome and time-consuming procedure. For instance, the prosthetist often is required to take apart a prosthetic device and then put it back together again, such as when correcting the device when a bushing wears out, when a new component is added, if a component breaks, or if the device becomes loose from wear. When the prosthetic device is reassembled, the adjustable joint or joints which have been disassembled must be reassembled and realigned. The alignment process for the Otto Bock joint, for example, requires settings in the anterior-posterior and the lateral-medial planes. In the past, the Otto Bock joint has been realigned by keeping track of the amount of rotation of each of the four set screws, although this is not always a desirable or foolproof method. Moreover, after reassembling the new prosthetic device, if an adjustable prosthetic link must be reset, the patient must walk with the new device to test whether the realignment is correct, and then through trial and error the device may be properly aligned.

The present invention takes the guess work out of the realignment procedure and provides a means for quickly and easily realigning an adjustable prosthetic joint.

SUMMARY OF THE INVENTION

Briefly, one embodiment of this invention provides an easily adjustable and realignable prosthetic joint interconnecting two members of a prosthetic limb, comprising a male part rigid with one of the members and a complementary female part rigid with the other of the two members. The male part includes a spherically convex base and a boss of substantially frustopyramidal configuration divergingly rising from the base. Two pairs of opposite sides of the boss form respective pairs of contact surfaces bisected by mutually orthogonal planes. The female part comprises an annular socket surrounding the boss, where the socket has a spherically concave ring surface complementary to and of the same radius of curvature as the base and in slidable engagement with the base. An adjustable abutment on the socket engages the contact surfaces for retaining the parts in a selected angular position within predetermined swing angles in the two pairs of planes. The adjustable joint further includes indexing means on a portion of one component visible for comparison of its angular position relative to the other component. The indexing means indicate the relative positions of the component parts in a plane that sets the posterior-anterior position and in a separate plane that sets the lateral-medial position of the joint. Further indexing means can indicate relative rotation of one component with respect to the other about a substantially vertical axis through the joint.

By using the indexing means of this invention, the prosthetist can record the relative positions of the components in three independent rotational directions so that the recorded information can be referred to later when realigning the component parts of the prosthetic joint. In this way, the realignment procedure can be accomplished quickly and accurately.

These and other aspects of the invention will be more fully understood by referring to the following detailed description and the accompanying drawings.

BRIEF DESCRIPTION OF THE DRAWINGS

FIG. 2 is an exploded side elevation view of the adjustable prosthetic link of this invention.

FIG. 3 is an end elevation view taken on line 3—3 of FIG. 2.

FIG. 4 is an end elevation view taken on line 4—4 of FIG. 2.

DETAILED DESCRIPTION

Figure 1:
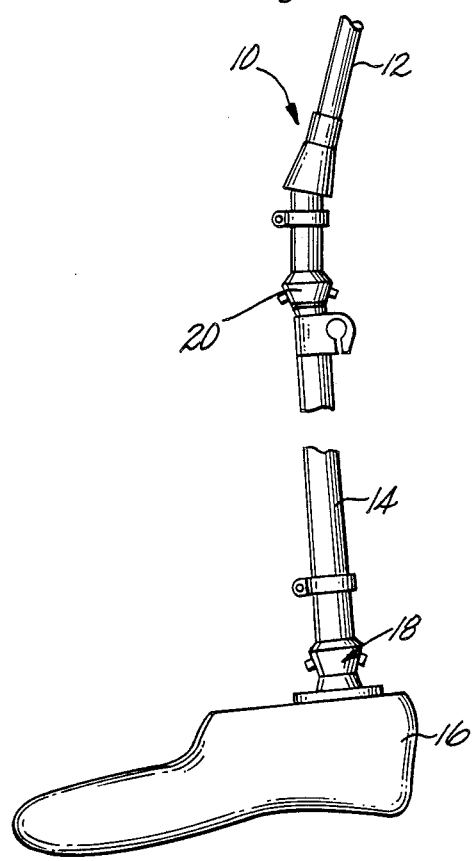
FIG. 1 is a fragmentary side elevation view showing a prosthetic limb using several adjustable links according to the principles of this invention.

FIG. 1 schematically illustrates an artificial limb having a thigh member 12, a lower leg member 14, and a prosthetic foot 16. The artificial limb is illustrated as an example only of various places where the adjustable prosthetic link of this invention can be used. For instance, one adjustable prosthetic link 18 can be used as an ankle joint between the lower leg member 14 and the prosthetic foot 16. Another adjustable prosthetic link 20 can be used above the lower leg member below an artificial knee joint, for example. FIGS. 2 through 7 illustrate an adjustable prosthetic link with self-alignment means according to principles of this invention which can be used as the prosthetic link 18 or 20, or which can be used at the joints in other prosthetic limbs. For instance, a typical prosthetic leg can have from one to four of such adjustable prosthetic links, which can include the ankle joint, a joint below the knee, a joint above the knee, and a hip joint, or various combinations of these prosthetic joints.

Referring to FIGS. 2 through 4, the adjustable prosthetic link of the invention comprises a male part 22 below a female part 24. The male part has a spherically convex base 26 rigid with an upper portion of a lower connector portion 28 of the male part. A central boss 30 of frustopyramidal configuration projects upwardly from the spherically convex base 26. The frustopyramid formed by the main portion of the boss is of square cross section and therefore has four uniform sides 30a, 30b, 30c, and 30d facing outwardly in four directions spaced apart by 90°. The four sides of the boss are contacted by separate set screws 32a, 32b, 32c, and 32d, which are carried at 90° intervals spaced apart around the bottom of the female part 24. These set screws are threaded into an annular socket 34 which projects outwardly and extends across the bottom of the female part 24. The annular socket extends below a tubular upper connector portion 35 of the female part 24. The annular socket has a spherically curved concave upper ring surface 36 having the same radius of curvature as the spherically curved base 26 of the male part 22. Thus, the spherical bottom surface 36 of the female member slides back and forth and can rotate on the spherical surface 26 of the male part. In the illustrated embodiment, the four sides of the frustopyramidal boss extend upwardly at angles of about 14° with respect to the vertical axis through the joint. The set screws 32 also extend along separate axes at about 14° with respect to a horizontal plane. Thus, each set screw can be rotated for tightening or loosening it along an axis approximately perpendicular to the confronting corresponding faces 30a–30d of the pyramidal boss 30.

Figure 5:
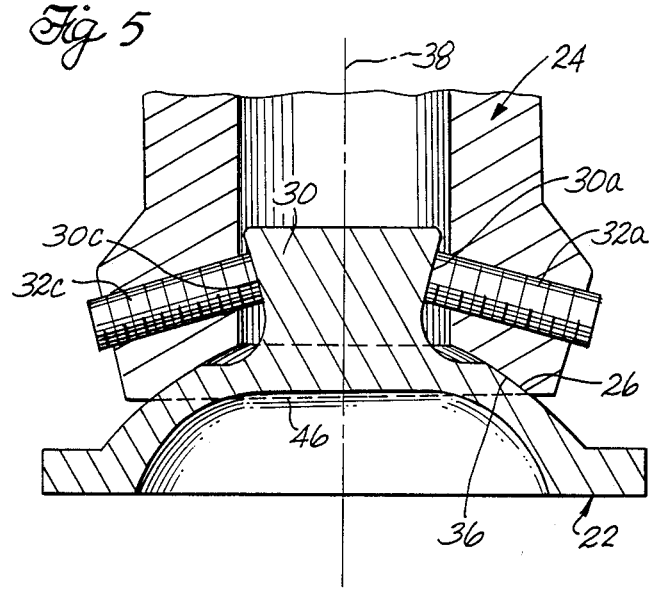
FIG. 5 is a cross sectional view of the assembled components of the adjustable prosthetic link.

FIG. 5 illustrates the male and female parts assembled to one another with the set screws 32 tightened against the corresponding faces of the boss 30. Upon loosening of a first pair of set screws on opposite sides of the boss, and a second pair of set screws perpendicular to the first pair, the female part can be swung out of line with respect to a vertical axis 38 through the male part. This allows the female part to rotate within a limited angular range relative to the male part for setting a first angular position of the two components in the anterior-posterior plane and for setting a second angular position in the medial-lateral plane. These are mutually orthogonal with respect to one another.

Further information as to the structure and function of the adjustable prosthetic link is disclosed in U.S. Pat. No. 3,659,294 to Glabiszewski and the related adjustable prosthetic link sold by Otto Bock of West Germany, which are incorporated herein by that reference.

In use, the male and female parts are aligned using indexing means on the male part for marking its alignment relative to the female part. The indexing means comprise a series of concentric rings permanently recessed as thin grooves formed in the convexly curved exterior contact surface 26 of the male part. The rings are preferably at uniformly spaced apart levels on the contact surface 26 and are concentric about the vertical axis 38 through the male part. In the preferred form of the invention there are four concentric rings 40a, 40b, 40c, and 40d of progressively wider diameter at intervals starting from just below the top of the contact surface and progressing to slightly above the maximum-diameter lower portion of the surface.

The indexing means further comprise four sets of straight radial lines at 90° intervals around the contact surface 26. Each set of lines extends radially outwardly from a corresponding flat face 30a–30d of the frustopyramidal boss and bisects the four concentric rings 40a–40d. Each set of radial lines preferably comprises a central radial line 42a, two radial lines 42b and 42c on opposite sides of the central line at approximately plus and minus 5° intervals, and two further radial lines 42d and 42e at further angular intervals of plus and minus 5°. The angles at which the radial lines extend are defined with respect to the vertical axis 38 through the center of the boss 30.

The indexing means also include four separate indexing marks 44 spaced apart at 90° intervals near the bottom center of the ring 34 extending around the bottom of the female part. Only one such indexing mark is shown in FIG. 2.

Figure 6:
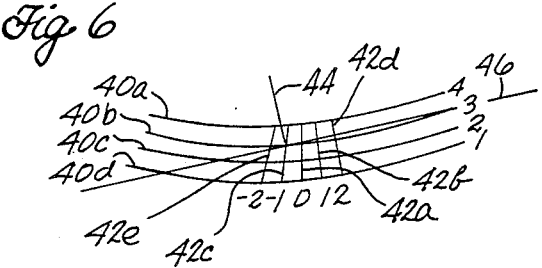
FIG. 6 is a schematic representation of the indexing means of this invention indicating one angular orientation.
Figure 7:
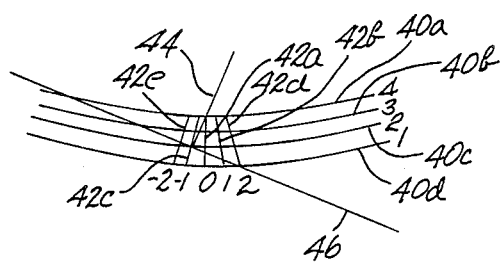
FIG. 7 is a schematic representation of the indexing means of this invention indicating another angular orientation.

In using the indexing means, the prosthetic joint can be taken apart by loosening the four set screws from contact with the four flat contact faces 30a–30d of the frustopyramidal boss 30. The female part then can be slipped over and removed from the male part. After reassembly of the prosthesis, the joint is reassembled by realigning the male and female parts in the same position they were in before taken apart. This can be accomplished quickly and easily using the indexing means. During the initial fitting of the prosthesis the male and female parts of the adjustable joint are initially connected together at proper relative angular positions by the prosthetist. This proper alignment is determined by the prosthetist by trial and error when testing the use of the prosthesis with the patient's proper walking gait, for example. The indexing means are then used to make a record of the correct alignment of the male and female parts of the adjustable joint. The concentric rings 40 are used to determine the angle through which the female part is rotated relative to the male part in two mutually orthogonal planes: the anterior-posterior plane and the lateral-medial plane. When adjusting the orientation of the two parts in these two planes, by rotating the two parts of the spherically curved contact surfaces 26 and 36, the flat bottom edge 46 of the female part is, in essence, rotated through an angle which intersects the concentric rings on the exterior lower surface of the male part. The indexing marks 44 at its point of intersection with the bottom edge 46 of the female part define points at four 90° intervals that may intersect corresponding ones of the concentric rings. There are at least two such intersections of the indexing marks 44 with concentric rings, at least one for the anterior-posterior plane and at least one for the lateral-medial plane. If the swing angle of the female part relative to the male part is relatively steep, the bottom of the ring on the female part may obscure all of the concentric rings, but only on one side of the device in each plane of rotation. The intersection points are then used to define the angular orientations of the male and female components in each of the two planes of movement which cooperate to provide a properly aligned joint. For instance, in FIG. 6 the intersection of the index mark 44 and the bottom 46 of the ring on the female part marks the third ring 40d in one plane of adjustment, and FIG. 7 shows the indexing mark 44 indicating the second concentric ring 40c in another plane of adjustment.

The radial lines 42a through 42e are used to indicate angular rotation of the male part relative to the female part, where such rotation is about the vertical axis 38 through the female part. In FIGS. 6 and 7 the indexing mark 44 at its point of intersection with the bottom edge 46 of the ring 34 identifies the radial line 42c (the −1 rotation) as the correct amount of rotation.

Thus, the prosthetist when initially setting the adjustable joint can record these measurements from the indexing means to indicate the proper relative positions of the male and female parts of the joint with respect to their angular orientations in the anterior-posterior plane, the lateral-medial plane, and their relative rotation about a vertical axis. When the prosthesis is later taken apart, it can be quickly and easily assembled using the recorded information to properly realign the male and female components of the adjustable joint.

What is claimed is:

1. In an adjustable link interconnecting two members of a prosthetic limb, comprising a male part rigid with one of said members and a complementary female part rigid with the other of said members, said male part including a spherically convex base and a boss of substantially frustopyramidal configuration divergingly rising from said base, two pairs of opposite sides of said boss forming respective pairs of contact surfaces bisected by mutually orthogonal planes, said female part comprising an annular socked surrounding said boss, said socket having a spherically concave ring surface complementary to and of the same radius of curvature as said base and in slidable engagement therewith, and adjustable abutment means on said socket engaging said surfaces for retaining said parts in a selected angular position within predetermined swing angles in said planes, the improvement comprising:

indexing means for aligning the male part relative to the female part comprising a plurality of radially spaced apart indexing lines permanently affixed to the spherically convex base of the male part, the indexing lines being concentric with a vertical axis through the boss, the indexing lines extending at different elevations on the base and being visible thereon for comparison of the angular position of the male part relative to the female part;

alignment means on the female part for use in indicating the position of the female part with respect to corresponding ones of the indexing lines visible on the base, so that the female part can be rotated on the base through swing angles in the anterior-posterior plane and in the lateral-medial plane and the respective swing angles can be identified by a comparison of the positions of the alignment means on the female part with said corresponding indexing lines on the base; and further indexing means indicating the relative rotation of one part with respect to the other about a substantially vertical axis through the joint.

2. Apparatus according to claim 1 in which the frustopyramidal boss is four-sided.

3. Apparatus according to claim 1 in which the abutment means comprise two pairs of set screws extending perpendicularly to the sides of the frustopyramid.

4. Apparatus according to claim 1 in which the indexing lines comprise concentric circles on the spherical surface extending at different elevations thereon, and the alignment means comprise a separate indexing mark on at least one side of the female member for use in marking its relative position with respect to one of said concentric circles.

5. Apparatus according to claim 1 in which the indexing means further include separate radial indexing lines intersecting the concentric circles to that positioning of the alignment means on the female part with respect to one of the radial indexing lines on the male part indicates rotation of one part relative to the other.

6. Apparatus according to claim 5 including four separate sets of said radial indexing lines, one set adjacent each of four 90 degree spaced apart sides of the male part of the device.

7. In an adjustable link interconnecting two members of a prosthetic limb, comprising a male part rigid with one of said members and a complementary female part rigid with the other of said members, said male part including a spherically convex base and a boss of substantially frustopyramidal configuration divergingly rising from said base, two pairs of opposite sides of said boss forming respective pairs of contact surfaces bisected by mutually orthogonal planes, said female part comprising an annular socket surrounding said boss, said socket having a spherically concave ring surface complementary to and of the same radius of curvature as said base, and in slidable engagement therewith, and adjustable abutment means on said socket engaging said surfaces for retaining said parts in a selected angular position within predetermined swing angles in said planes, the improvement comprising:

indexing means for aligning the male part relative to the female part comprising a plurality of radially spaced apart indexing lines permanently affixed to the spherically convex base of the male part, the indexing lines being concentric with a vertical axis through the boss, the indexing lines extending at different elevations on the base and being visible thereon for comparison of the angular position of the male part relative to the female part; and alignment means on the female part for use in indicating the position with respect to corresponding ones of the indexing lines visible on the base, so that the female part can be rotated on the base through swing angles in the anterior-posterior plane and in the lateral-medial plane and the respective swing angles can be identified by a comparison of the positions of the alignment means on the female part with said corresponding indexing lines on the base.

8. Apparatus according to claim 7 in which the alignment means comprise a pair of indexing marks spaced 90° apart on the female part for alignment with corresponding ones of the concentric indexing lines for indicating the relative angular position of the male and female parts of the device.

9. Apparatus according to claim 7 in which the frustopyramidal boss is four-sided.

10. Apparatus according to claim 7 in which the abutment means comprise two pairs of set screws extending perpendicularly to the sides of the frustopyramid.

11. Apparatus according to claim 7 in which the indexing lines comprise concentric circles on the spherical surface extending at different elevations thereon, and the alignment means comprise a separate indexing mark on at least one side of the female member for use in marking its relative position with respect to one of said concentric circles.

12. Apparatus according to claim 7 in which the indexing means further include separate radial indexing lines intersecting the concentric circles to that positioning of the alignment means on the female part with respect to one of the radial indexing lines on the male part indicates rotation of one part relative to the other.

13. Apparatus according to claim 12 including four separate sets of said radial indexing lines, one set adjacent each of the four 90 degree spaced apart of the male part of the device.

* * * * *

UNITED STATES PATENT AND TRADEMARK OFFICE
CERTIFICATE OF CORRECTION

PATENT NO. : 4,969,911
DATED : November 13, 1990
INVENTOR(S) : Ted J. Greene

It is certified that error appears in the above-identified patent and that said Letters Patent is hereby corrected as shown below:

Column 3, line 45, after "of" and before "invention" change "the" to -- this --.

Column 5, line 64, after "annular" change "socked" to -- socket --.

Column 6, line 40, after "circles" change "to" to -- so --.

Column 8, line 20, after "apart" and before "of" insert -- sides --.

Signed and Sealed this

Twenty-first Day of April, 1992

Attest:

HARRY F. MANBECK, JR.

*Attesting Officer*  *Commissioner of Patents and Trademarks*